United States Patent
Iisaku et al.

(10) Patent No.: US 7,912,175 B2
(45) Date of Patent: Mar. 22, 2011

(54) X-RAY CT APPARATUS AND X-RAY CT SCANNING METHOD

(75) Inventors: Shinichi Iisaku, Tokyo (JP); Junko Sekiguchi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 232 days.

(21) Appl. No.: 11/956,873

(22) Filed: Dec. 14, 2007

(65) Prior Publication Data
US 2008/0292045 A1 Nov. 27, 2008

(30) Foreign Application Priority Data
Dec. 18, 2006 (JP) ................. 2006-339853

(51) Int. Cl.
*A61B 6/03* (2006.01)
(52) U.S. Cl. .............................. 378/8; 378/51
(58) Field of Classification Search ............... 378/4, 8, 378/62; 600/425, 431
See application file for complete search history.

(56) References Cited

U.S. PATENT DOCUMENTS

| | | |
|---|---|---|
| 5,459,769 A | 10/1995 | Brown |
| 5,686,061 A | 11/1997 | Li et al. |
| 6,188,744 B1 * | 2/2001 | Shinohara et al. ............... 378/8 |
| 2004/0082846 A1 * | 4/2004 | Johnson et al. ............... 600/410 |
| 2005/0147198 A1 * | 7/2005 | Kiyono .............................. 378/4 |
| 2006/0034419 A1 * | 2/2006 | Nishide et al. .................. 378/15 |
| 2006/0140336 A1 * | 6/2006 | Russinger et al. ............... 378/4 |

FOREIGN PATENT DOCUMENTS

| | | |
|---|---|---|
| DE | 102005024323 A1 * | 8/2006 |
| JP | 09-327454 | 12/1997 |

* cited by examiner

*Primary Examiner* — Edward J Glick
*Assistant Examiner* — John M Corbett
(74) *Attorney, Agent, or Firm* — Armstrong Teasdale LLP

(57) ABSTRACT

The present invention is directed to realize an X-ray CT apparatus for properly performing contrast imaging. An X-ray CT apparatus includes an imaging unit and a control unit for controlling the imaging unit. The control unit includes: a first control unit for performing a monitoring scan to monitor arrival of a contrast agent at a region of interest in a start position of a main scan in an imaging range of the main scan that is set along the body axis of the subject or a first monitoring position that is set before the start position in a scan progress direction and, on arrival of the contrast agent, starting the main scan; and a second control unit for monitoring whether or not the contrast agent has reached a region of interest in a second monitoring position provided on the forward side of the start position of the main scan in the imaging range in the scan progress direction on arrival of the main scan at the second monitoring position, when the contrast agent has reached the second monitoring position, continuing the main scan and, when the contrast agent has not reached the second monitoring position yet, performing a monitoring scan for monitoring arrival of the contrast agent.

20 Claims, 6 Drawing Sheets

X-RAY CT APPARATUS AND X-RAY CT SCANNING METHOD

CROSS REFERENCE TO RELATED APPLICATIONS

This application claims the benefit of Japanese Patent Application No. 2006-339853 filed Dec. 18, 2006.

BACKGROUND OF THE INVENTION

The present invention relates to an X-ray CT (Computed Tomography) apparatus and, more particularly, to an X-ray CT apparatus for capturing an image of a subject in which a contrast agent is injected.

In an X-ray CT apparatus for capturing an image of a subject in which a contrast agent is injected, prior to a main scan, a helical scan is started synchronously with arrival of the contrast agent at a region of interest (ROI) in a monitoring scan executed with a dose lower than that of the main scan. In this case, after the scan starts, the helical scan with constant progress speed is performed (refer to, for example, Japanese Unexamined Patent Publication No. Hei09 (1997)-327454).

SUMMARY OF THE INVENTION

In an X-ray CT apparatus using a combination of a multiple-channel X-ray detector or a plane X-ray detector and a cone beam X-ray, because of increase in the helical pitch and increase in the detector width in the body axis direction due to three-dimensional image reconstruction, the progress speed of the helical scan is increasing. Consequently, there is a case such that a helical scan is faster than a contrast agent moving with blood flow, and contrast imaging cannot be performed properly.

An object of the present invention is to realize an X-ray CT apparatus for properly performing contrast imaging.

The present invention for solving the problem provides an X-ray CT apparatus including: an imaging unit for reconstructing an image on the basis of projection data obtained by scanning a subject in which a contrast agent is injected with an X ray; and a control unit for controlling the imaging unit. The control unit includes: a first control unit for performing a monitoring scan to monitor arrival of a contrast agent at a region of interest in a start position of a main scan in an imaging range of the main scan that is set along the body axis of the subject or a first monitoring position that is set before the start position in a scan progress direction and, on arrival of the contrast agent, starting the main scan; and a second control unit for monitoring whether or not the contrast agent has reached a region of interest in a second monitoring position provided on the forward side of the start position of the main scan in the imaging range in the scan progress direction on arrival of the main scan at the second monitoring position, when the contrast agent has reached the second monitoring position, continuing the main scan and, when the contrast agent has not reached the second monitoring position yet, performing a monitoring scan for monitoring arrival of the contrast agent.

The control unit monitors arrival of the contrast agent by detecting the contrast agent by using an image obtained by reconstructing a slice image in the monitoring position. The contrast agent is detected on the basis of a CT number in the region of interest. The second control unit assigns a higher priority to the image reconstruction in the second monitoring position than image reconstruction in the other imaging range.

As the second monitoring position, a plurality of monitoring positions are set at intervals in the body axis direction of the subject. A plurality of regions of interest in which arrival of the contrast agent is monitored can be set. The X-ray is a cone beam X-ray. The scan is a helical scan.

According to the present invention, an X-ray CT apparatus includes: an imaging unit for reconstructing an image on the basis of projection data obtained by scanning a subject in which a contrast agent is injected with an X ray; and a control unit for controlling the imaging unit. The control unit includes: a first control unit for performing a monitoring scan to monitor arrival of a contrast agent at a region of interest in a start position of a main scan in an imaging range of the main scan that is set along the body axis of the subject or a first monitoring position that is set before the start position in a scan progress direction and, on arrival of the contrast agent, starting the main scan; and a second control unit for monitoring whether or not the contrast agent has reached a region of interest in a second monitoring position provided on the forward side of the start position of the main scan in the imaging range in the scan progress direction on arrival of the main scan at the second monitoring position, when the contrast agent has reached the second monitoring position, continuing the main scan and, when the contrast agent has not reached the second monitoring position yet, performing a monitoring scan for monitoring arrival of the contrast agent. Thus, the X-ray CT apparatus properly performing contrast imaging can be realized.

DETAILED DESCRIPTION OF THE INVENTION

Figure 1:
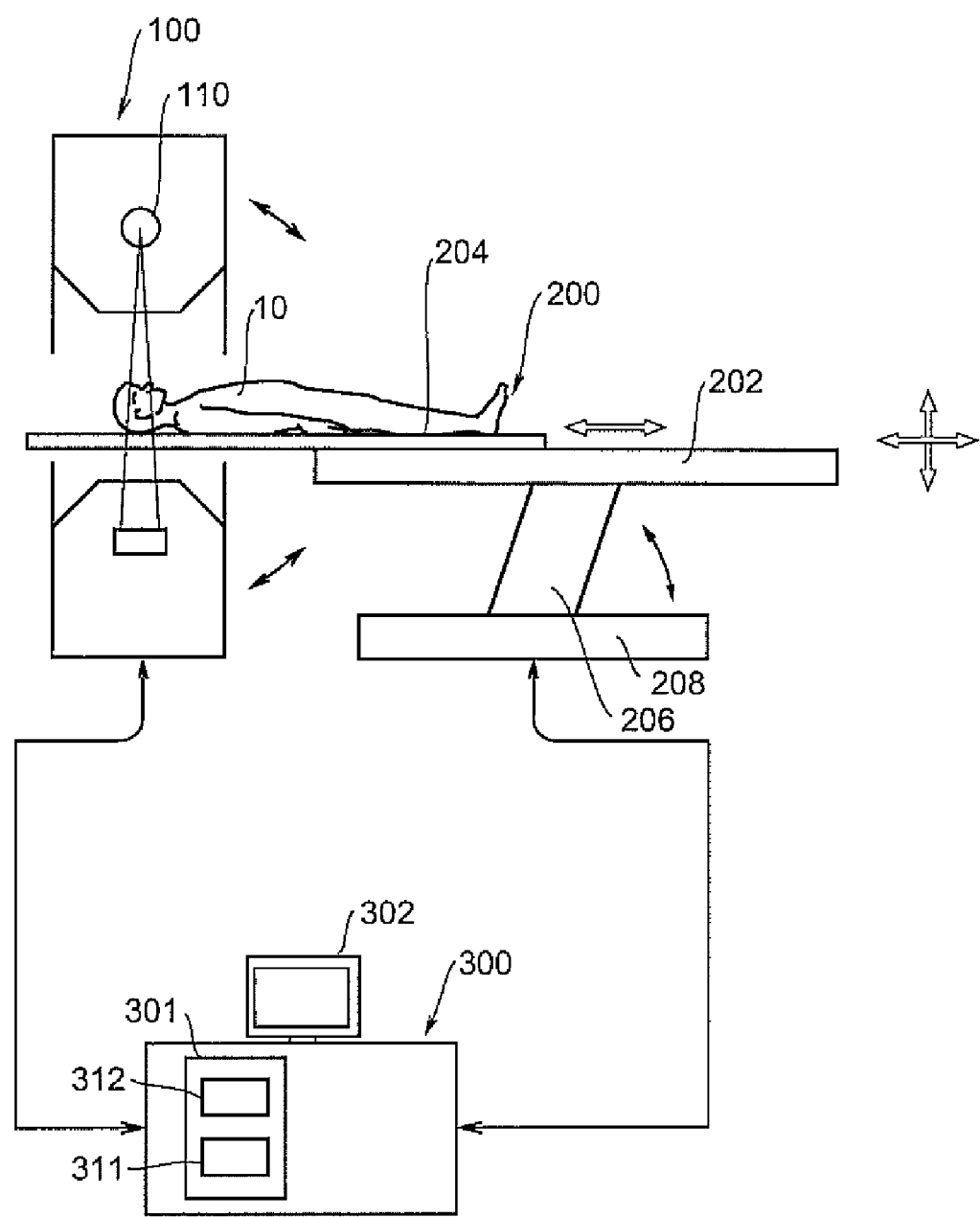
FIG. 1 is a diagram showing the configuration of an X-ray CT apparatus as an example of the best mode for carrying out the invention.

A best mode for carrying out the invention will be described hereinbelow with reference to the drawings. The present invention is not limited to the best mode for carrying out the invention. FIG. 1 shows a schematic configuration of an X-ray CT apparatus. The apparatus is an example of the best mode for carrying out the invention. By the configuration of the apparatus, an example of the best mode for carrying out the invention related to the X-ray CT apparatus will be described. By the operation of the apparatus, an example of the best mode for carrying out the invention related to a scan control method will be described.

The apparatus has a gantry 100, a table 200, and an operator console 300. The gantry 100 scans a subject 10 conveyed by the table 200 with an X-ray irradiating/detecting apparatus 110 to collect a plurality of views of projection data, and inputs the projection data to the operator console 300.

The operator console 300 reconstructs an image on the basis of the projection data input from the gantry 100, and displays a reconstructed image on a display 302. The image reconstruction is performed by a dedicated computer in the operator console 300. The computer for image reconstruction, the gantry 100, and the table 200 are examples of the imaging unit in the present invention.

The operator console 300 controls the operation of the gantry 100 and the table 200. The control is performed by the dedicated computer in the operator 300. The computer includes a control unit 301 in the invention. The control unit 301 also includes a first control unit 311 and a second control unit 312 in the invention. The control unit 301 also controls the image reconstruction.

Under control of the operator console 300, the gantry 100 performs a scan with predetermined scan parameters, and the table 200 positions the subject 10 so that a predetermined region is scanned. The positioning is performed by adjusting the height of a top board 202 and the horizontal travel distance of a cradle 204 on the top board by a built-in position adjusting mechanism.

By performing a scan in a state where the cradle 204 is stopped, an axial scan can be performed. By continuously performing a scan a plurality of times while successively moving the cradle 204, a helical scan can be conducted. By performing a scan in each of stop positions while intermittently moving the cradle 204, a cluster scan can be carried out.

The height of the top board 202 is adjusted by making a stay 206 swing around the attachment part to a base 208 around the center. By the swing of the stay 206, the top board 202 is displaced in the vertical and horizontal directions. The cradle 204 moves in the horizontal direction on the top board 202, thereby cancelling off the displacement in the horizontal direction of the top board 202. Depending on scan parameters, a scan is performed in a state where the gantry 100 is tilted. The gantry 100 is tilted by a built-in tilting mechanism.

Figure 2:
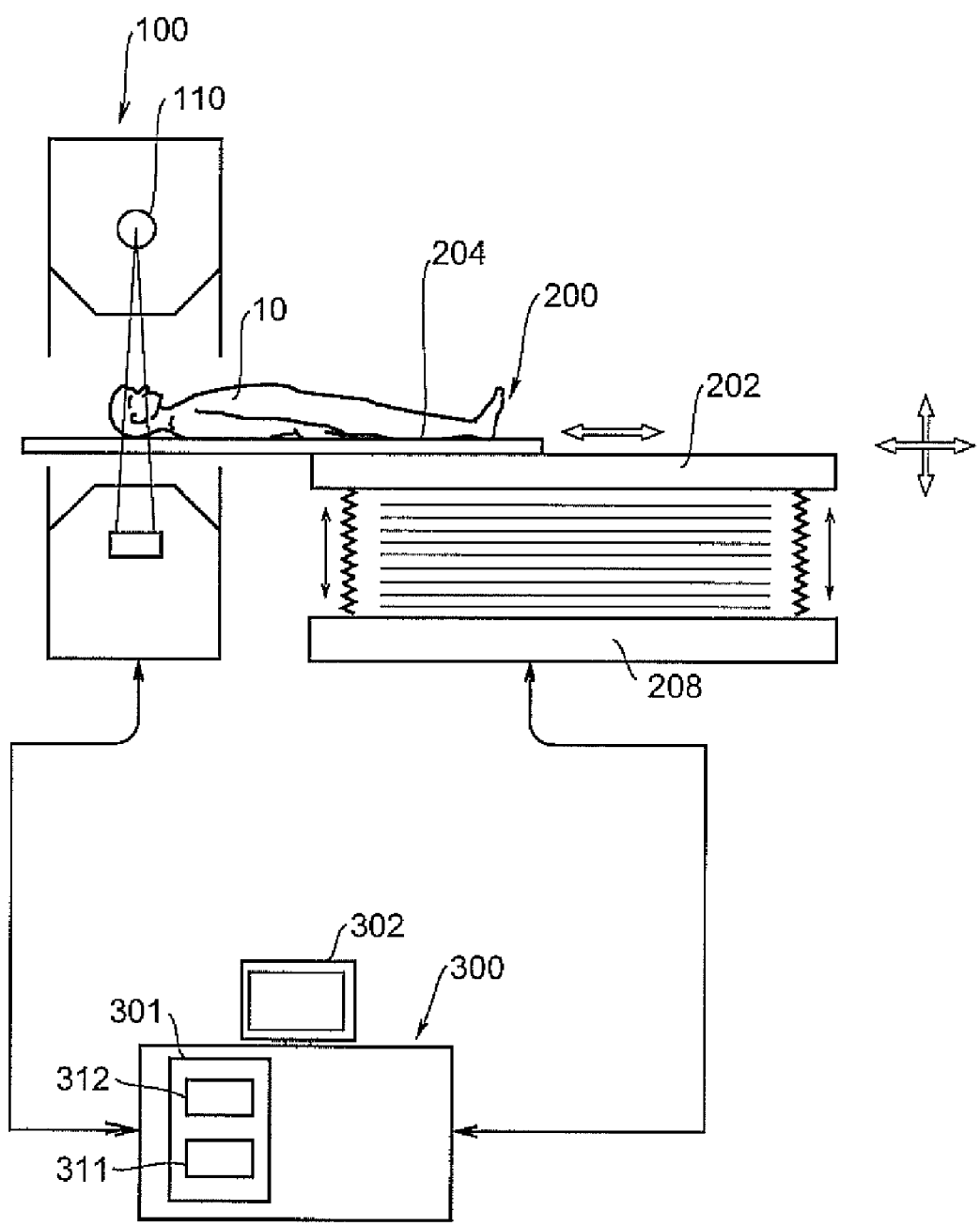
FIG. 2 is a diagram showing the configuration of an X-ray CT apparatus as an example of the best mode for carrying out the invention.

The table 200 may be of a type in which the top board 202 is moved vertically to the base 208 as shown in FIG. 2. The top board 202 is moved in the vertical direction by a built-in lifting mechanism. In the table 200, horizontal travel of the top board 202 accompanying the vertical movement does not occur.

Figure 3:
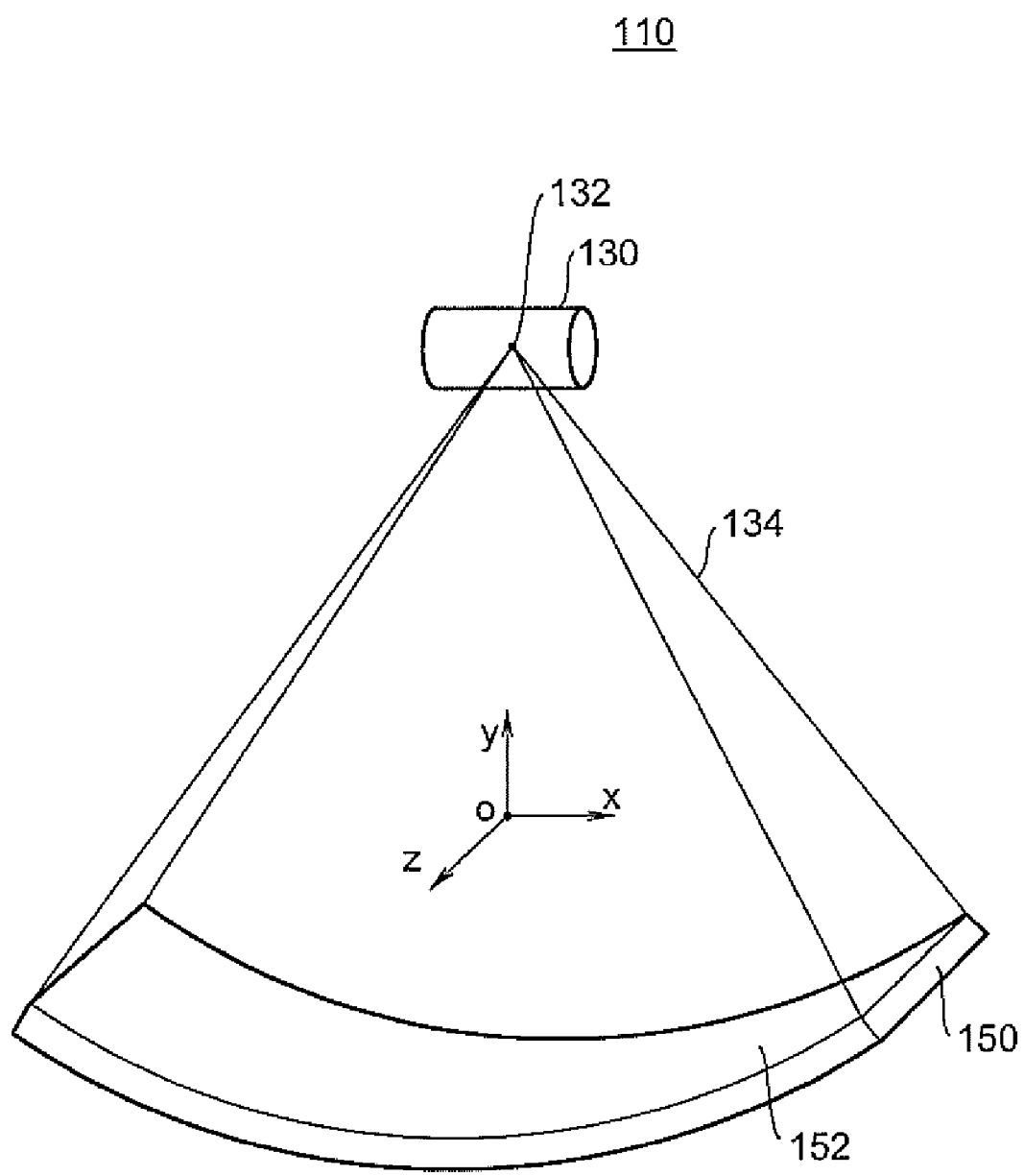
FIG. 3 is a diagram showing the configuration of an X-ray irradiating/detecting apparatus.

FIG. 3 schematically shows the configuration of an X-ray irradiating/detecting apparatus 110. The X-ray irradiating/detecting apparatus 110 detects an X-ray 134 emitted from a focal point 132 of an X-ray tube 130 by an X-ray detector 150.

The X-ray 134 is formed as a cone-beam or fan-beam X-ray by a not-shown collimator. The X-ray detector 150 has an X-ray entrance plane 152 which extends two-dimensionally in correspondence with the spread of an X-ray. The X-ray entrance plane 152 is curved so as to construct a part of a cylinder. The center axis of the cylinder passes through the focal point 132.

The X-ray irradiating/detecting apparatus 110 rotates around the center axis passing the center of imaging, that is, isocenter O. The center axis is parallel with the center axis of the cylinder a part of which is formed by the X-ray detector 150.

The direction of the center axis of rotation is set as the z direction, the direction extending from the isocenter O to the focal point 132 is set as the y direction, and the direction perpendicular to the z direction and the y direction is set as the x direction. The x, y, and z axes are three axes of a rotation coordinate system using the z axis as a center.

Figure 4:
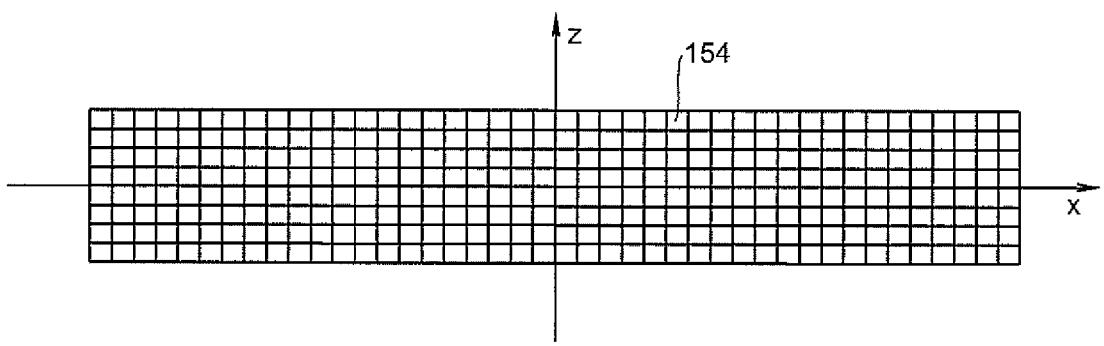
FIG. 4 is a diagram showing the configuration of an X-ray entrance plane of an X-ray detector.

FIG. 4 is a schematic plan view of the x-ray entrance plane 152 of the X-ray detector 150. In the X-ray entrance plane 152, detection cells 154 are arranged two-dimensionally in the x and z directions. That is, the X-ray entrance plane 152 is a two-dimensional array of the detection cells 154. In the case of using a fan-beam X-ray, the X-ray entrance plane 152 may be a one-dimensional array of the detection cells 154.

Each of the detection cells 154 serves as a detection channel of the X-ray detector 150. Accordingly, the X-ray detector 150 takes the form of a multi-channel X-ray detector. The detection cell 154 is formed by, for example, a combination of a scintillator and a photo diode.

Figure 5:
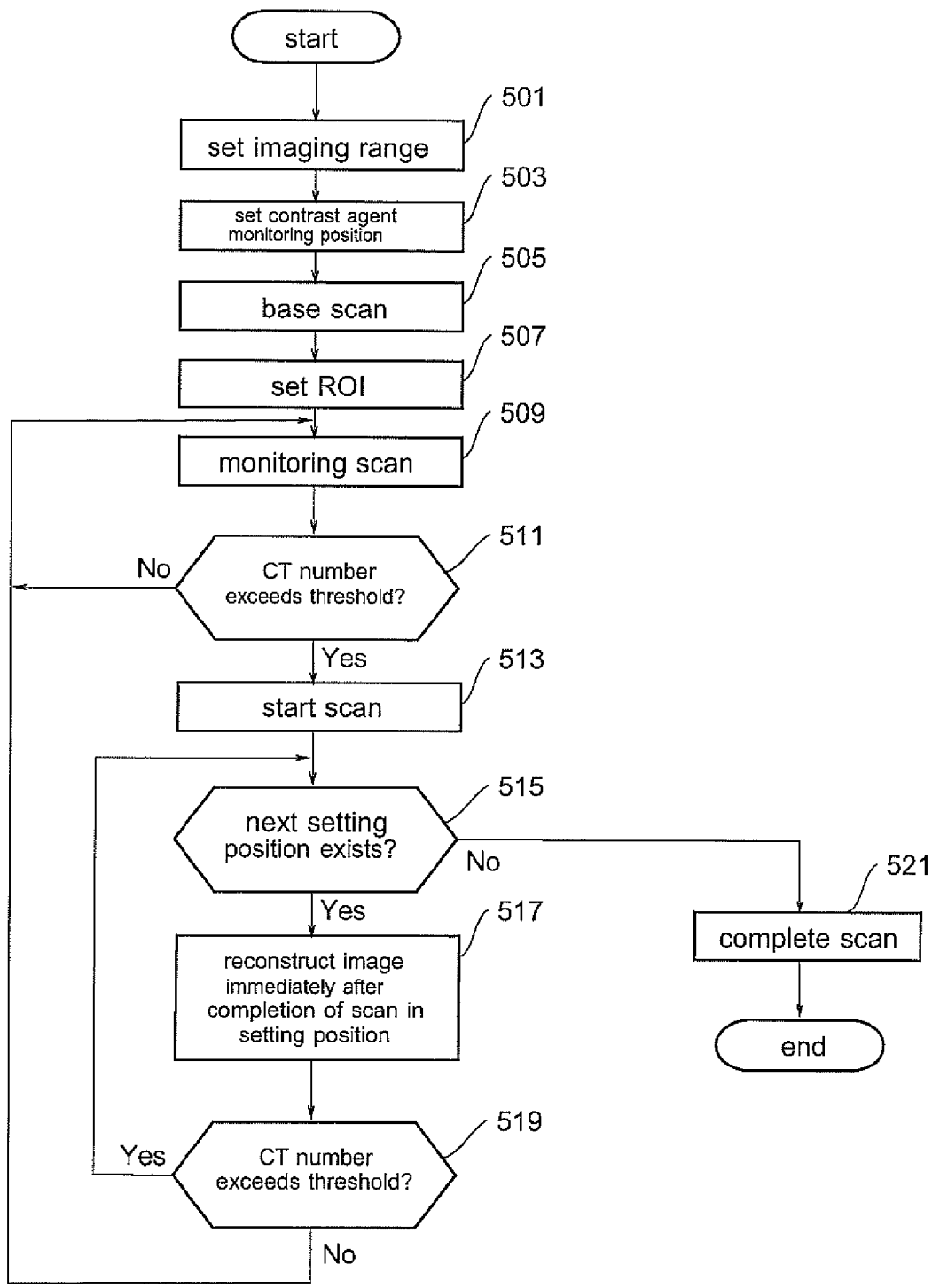
FIG. 5 is a flowchart showing operations of contrast imaging.
Figure 6:
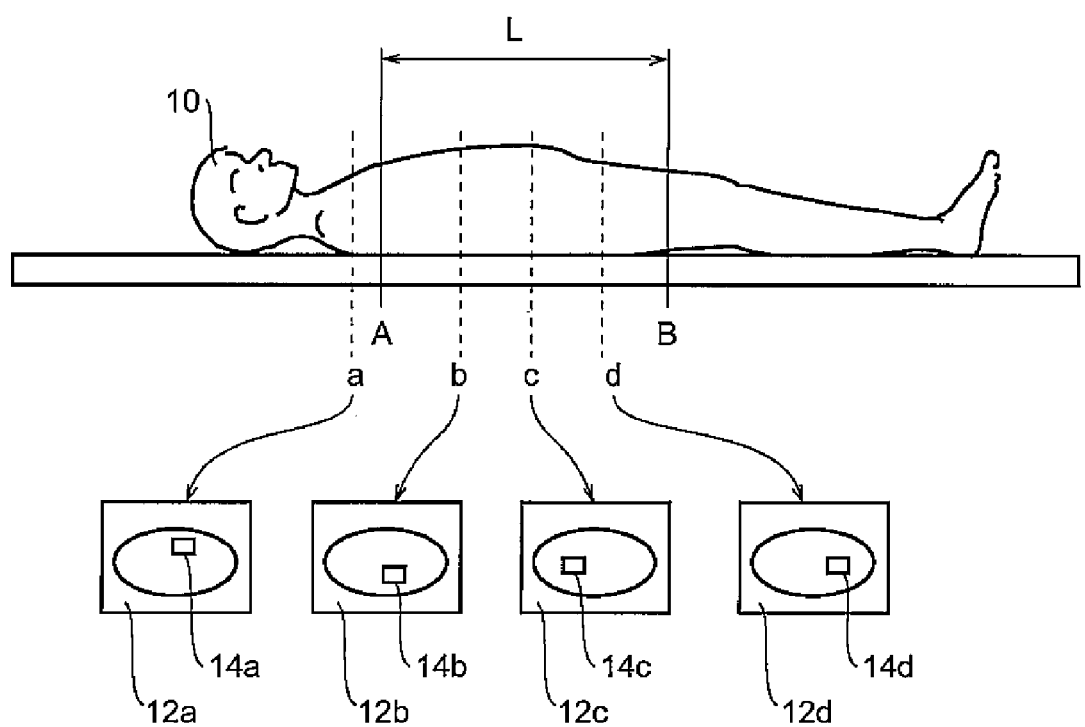
FIG. 6 is a diagram showing an imaging range and contrast agent monitoring positions.

The contrast imaging of the apparatus will be described. FIG. 5 is a flowchart of the contrast imaging. The contrast imaging is performed under control of the operator console 300. As shown in FIG. 5, an imaging range is set in step 501. The imaging range is set by the operator with the operator console 300. As a result, for example, an imaging range L as shown in FIG. 6 is set. The imaging range L is a range from the position A to the position B on the body axis of the subject 10.

In step 503, a contrast agent monitoring position is set. The contrast agent monitoring position is set by the operator with the operator console 300 or may be automatically set in association with the setting of the imaging range L. For example, contrast agent monitoring positions a, b, c, and d as shown in FIG. 6 are set. Although the case where the number of contrast agent monitoring positions is four is described here, the number of contrast agent monitoring positions to be set is not limited to four but may be proper number. Hereinbelow, the contrast agent monitoring position will be also simply called a monitoring position.

The monitoring position "a" is the uppermost position of a passage of the contrast agent, and the monitoring positions "b", "c", and "d" are sequentially on the downstream of the monitoring position "a". The monitoring position "a" is set out of the imaging range, and the monitoring positions "b", "c", and "d" are set in the imaging range. The monitoring position "a" may be set in the head position A of the imaging range. The monitoring position "a" corresponds to a first monitoring position of the invention, and the monitoring positions "b", "c", and "d" correspond to second monitoring positions of the invention.

In step 505, a base scan is performed. The base scan is performed at each of the monitoring positions "a", "b", "c", and "d" in a state where the contrast agent is not injected to the subject 10, thereby obtaining slice images 12$a$, 12$b$, 12$c$, and 12$d$ at the monitoring positions "a", "b", "c", and "d", respectively.

In step 507, an ROI is set. The ROI setting is made by the operator using the operator console 300. For example, regions of interest (ROI) 14$a$, 14$b$, 14$c$, and 14$d$ are set for the slice images 12$a$, 12$b$, 12$c$, and 12$d$, respectively. The regions of interest (ROI) are regions in the body through which the contrast agent is expected to pass. Although one region of interest is set for each of the slice images, a plurality of regions of interest may be set for each slice image. The number of regions of interest may vary among slice images.

In step 509, a monitoring scan is performed. The monitoring scan is a scan performed with a dose lower than that of the main scan which will be described later, in order to monitor arrival of the contrast agent. The monitoring scan starts concurrently with injection of the contrast agent into the subject 10. The monitoring scan is performed, first, at the monitoring position "a", thereby obtaining the slice image 12$a$.

In step 511, whether a CT number exceeds a threshold or not is determined by the operator console 300. The CT number is of the ROI 14$a$. The threshold is determined so as to be larger than the CT number when the contrast agent does not flow in the ROI 14$a$ and smaller than the CT number when the contrast agent flows in the ROI 14$a$.

When the CT number does not exceed the threshold, the program returns to step 509 and the monitoring scan is continued. The slice image 12a is updated and the CT number of the updated slice image 12a undergoes the determination in step 511. For the time the CT number does not exceed the threshold, the operations in steps 509 and 511 are repeated.

When the contrast agent reaches the monitoring position "a" and the CT number in the ROI 14a exceeds the threshold, it is determined in step 511 that the CT number exceeds the threshold. That is, arrival of the contrast agent at the monitoring position "a" is detected. By detecting the arrival of the contrast agent, the program moves to step 513.

In step 513, the main scan is started. The main scan is a scan for acquiring a slice image actually used for diagnosis or the like. A helical scan starts from the head of the imaging range L. In parallel with the scan, image reconstruction is also performed. By the helical scan, the scan whose scan position changes from one end A to the other end B of the imaging range L is performed. The scan position changes continuously. The first control unit 311 controls from the start of the monitoring scan to the start of the main scan.

In place of the helical scan, the cluster scan may be conducted. In the case of the cluster scan, the scan position changes step by step. Although the example using the helical scan will be described below, the description is similar to that of the cluster scan.

In step 515, whether there is the next monitoring position or not is determined. Since the next monitoring position "b" is set, the program moves to step 517. In step 517, immediately after completion of the scan in the monitoring position "b", image reconstruction is performed. That is, prior to the other images which are reconstructed in parallel until then, the slice image 12b is reconstructed. As a result, the slice image 12b in the monitoring position "b" can be obtained without delay.

In step 519, whether the CT number exceeds the threshold or not is determined. The determination is made with respect to the ROI 14b of the slice image 12b. When a plurality of ROI 14b are set, whether any of the CT numbers exceeds the threshold or not is determined. Alternatively, whether an average value of the CT numbers of a plurality of ROI exceeds the threshold or not may be determined. In the following description, it will be applied similarly.

When the CT number of the ROI 14b does not exceed the threshold, the program returns to the monitoring scan of step 509. The monitoring scan in step 509 is performed in the monitoring position "b". The slice image 12b is updated and, with respect to the image, the CT number in the ROI 14b exceeds the threshold or not is determined in step 511.

For the time the CT number does not exceed the threshold, the monitoring scan is continued and, with respect to each of slice images obtained, the CT number in the ROI 14b is determined on the basis of the threshold. When the CT number does not exceed the threshold, it shows that the contrast agent has not reached the monitoring position. In such a case, the program waits for the arrival of the contrast agent while performing the monitoring scan in the monitoring position "b".

When the contrast agent reaches the monitoring position "b" and the CT number in the ROI 14b exceeds the threshold, based on the determination in step 511, the program moves to step 513 and starts the scan. In such a manner, the helical scan restarts from the monitoring position "b".

On the other hand, in the case where it is determined in step 519 that the CT number in the ROI 14b exceeds the threshold, the program returns to step 515 and determines whether there is the next monitoring position or not. Since the next monitoring position "c" is set, in step 517, the slice image 12c in the monitoring position "c" is reconstructed. In step 519, whether the CT number of the ROI 14c exceeds the threshold or not is determined.

In the following, with respect to the monitoring positions "c" and "d", operations similar to those for the monitoring position "b" are performed. When there is not next monitoring position, in step 521, the scan is performed to the end point of the imaging range L, and completes. As described above, whether the contrast agent has reached a monitoring position or not is determined during a scan. When the contrast agent has not reached a monitoring position, the program waits for arrival of the contrast agent while performing the monitoring scan. After confirming that the contrast agent has reached a monitoring position, the helical scan is continued. Consequently, the contrast imaging can be properly performed in the whole imaging range L. Monitoring in the monitoring positions "b", "c", and "d" and control of a scan according to the result of monitoring is performed by the second control unit 312.

Successive detection of the contrast agent during a scan may be automatically performed in many positions in the imaging range without presetting the monitoring positions. When the monitoring agent has not reached a monitoring position, the monitoring scan may be performed in the position.

The invention claimed is:

1. An X-ray computed tomography (CT) apparatus comprising:
    an imaging unit for reconstructing an image on the basis of projection data obtained by scanning a subject in which a contrast agent is injected with an X ray; and
    a control unit for controlling the imaging unit,
        wherein the control unit comprises:
        a first control unit for performing a first monitoring scan in a first monitoring position to monitor an arrival of the contrast agent at a region of interest in a start position of a main scan in an imaging range of the main scan that is set along a body axis of the subject or the first monitoring position that is set before the start position in a scan progress direction and, on the arrival of the contrast agent, starting the main scan; and
        a second control unit for monitoring whether the contrast agent has reached the region of interest in a second monitoring position provided on the forward side of the start position of the main scan in the imaging range in the scan progress direction on arrival of the main scan at the second monitoring position, stopping the main scan and performing a second monitoring scan in the second monitoring position until the contrast agent reaches the second monitoring position, and restarting the main scan when the contrast agent reaches the second monitoring position, wherein the first monitoring scan and the second monitoring scan are performed with a dose that is lower than a dose with which the main scan is performed.

2. The X-ray CT apparatus according to claim 1, wherein the control unit monitors arrival of the contrast agent by detecting the contrast agent by using an image obtained by reconstructing a slice image in the first monitoring position.

3. The X-ray CT apparatus according to claim 2, wherein the contrast agent is detected on the basis of a CT number in the region of interest.

4. The X-ray CT apparatus according to claim 3, wherein the second control unit assigns a higher priority to the image reconstruction in the second monitoring position than image reconstruction in the other imaging range.

5. The X-ray CT apparatus according to claim 1, wherein the second control unit assigns a higher priority to the image reconstruction in the second monitoring position than image reconstruction in the other imaging range.

6. The X-ray CT apparatus according to claim 1, wherein, as the second monitoring position, a plurality of monitoring positions are set at intervals in the body axis direction of the subject.

7. The X-ray CT apparatus according to claim 1, wherein a plurality of regions of interest in which arrival of the contrast agent is monitored can be set.

8. The X-ray CT apparatus according to claim 1, wherein the X-ray is a cone beam X-ray.

9. The X-ray CT apparatus according to claim 1, wherein the scan is a helical scan.

10. The X-ray CT apparatus according to claim 1, further comprising a display unit for displaying the reconstructed image.

11. An X-ray computed tomography (CT) imaging method comprising:
    injecting a contrast agent to a subject;
    performing a first monitoring scan in a first monitoring position for monitoring an arrival of the contrast agent at a region of interest in a start position of a main scan in an imaging range of the main scan that is set along a body axis of the subject or the first monitoring position that is set before the start position in a scan progress direction;
    starting the main scan on the arrival of the contrast agent;
    monitoring whether the contrast agent has reached a region of interest in a second monitoring position provided on the forward side of the start position of the main scan in the imaging range in the scan progress direction on arrival of the main scan at the second monitoring position;
    controlling the main scan by stopping the main scan unit and performing a second monitoring scan in the second monitoring position until the contrast agent reaches the second monitoring position, continuing the main scan when the contrast agent reaches the second monitoring position; and
    reconstructing an image on the basis of projection data obtained by the main scan of the subject,
    wherein the first monitoring scan and the second monitoring scan are performed with a dose that is lower than a dose with which the main scan is performed.

12. The X-ray CT imaging method according to claim 11, wherein said monitoring scan monitors arrival of the contrast agent by detecting the contrast agent by using an image obtained by reconstructing a slice image in the first monitoring position.

13. The X-ray CT scanning method according to claim 12, wherein the contrast agent is detected on the basis of a CT number in the region of interest.

14. The X-ray CT scanning method according to claim 13, wherein said step for reconstructing including reconstructing an image in a higher priority of the second monitoring position image than of the other imaging range.

15. The X-ray CT scanning method according to claim 12, wherein said step for reconstructing including reconstructing an image in a higher priority of the second monitoring position image than of the other imaging range.

16. The X-ray CT scanning method according to claim 11, wherein, as the second monitoring position, a plurality of monitoring positions are set at intervals in the body axis direction of the subject.

17. The X-ray CT scanning method according to claim 11, wherein a plurality of regions of interest in which arrival of the contrast agent is monitored.

18. The X-ray CT scanning method according to claim 11, wherein the X-ray is a cone beam X-ray.

19. The X-ray CT scanning method according to claim 11, wherein the scan is a helical scan.

20. The X-ray CT scanning method according to claim 11, further comprising displaying the reconstructed image on a display unit.

* * * * *